(12) United States Patent
Rasparini et al.

(10) Patent No.: US 8,912,327 B2
(45) Date of Patent: Dec. 16, 2014

(54) PROCESS FOR THE PRODUCTION OF SITAGLIPTIN

(75) Inventors: Marcello Rasparini, Cura Carpignano (IT); Roberto Rocco Tufaro, Sozzago (IT); Cosima Minelli, Somma Lombardo (IT)

(73) Assignee: Chemo Iberica, S.A., Barcelona (ES)

( * ) Notice: Subject to any disclaimer, the term of this patent is extended or adjusted under 35 U.S.C. 154(b) by 0 days.

(21) Appl. No.: 14/114,781

(22) PCT Filed: May 4, 2012

(86) PCT No.: PCT/EP2012/058221
§ 371 (c)(1),
(2), (4) Date: Oct. 30, 2013

(87) PCT Pub. No.: WO2012/150328
PCT Pub. Date: Nov. 8, 2012

(65) Prior Publication Data
US 2014/0081026 A1    Mar. 20, 2014

(30) Foreign Application Priority Data

May 5, 2011  (IT) .............................. MI2011A0765

(51) Int. Cl.
| | | |
|---|---|---|
| *C07D 471/04* | (2006.01) | |
| *C07D 487/04* | (2006.01) | |
| *C07D 263/26* | (2006.01) | |
| *C07C 67/30* | (2006.01) | |
| *C07C 263/12* | (2006.01) | |
| *C07C 269/02* | (2006.01) | |
| *C07C 269/06* | (2006.01) | |
| *C07C 69/65* | (2006.01) | |
| *C07C 69/612* | (2006.01) | |

(52) U.S. Cl.
CPC ............ *C07D 487/04* (2013.01); *C07D 263/26* (2013.01); *C07C 67/30* (2013.01); *C07C 263/12* (2013.01); *C07C 269/02* (2013.01); *C07C 269/06* (2013.01); *C07C 69/65* (2013.01); *C07C 69/612* (2013.01)
USPC ........................................................ 544/350

(58) Field of Classification Search
CPC .................................................... C07D 257/10
See application file for complete search history.

(56) References Cited

FOREIGN PATENT DOCUMENTS

| WO | 03004498 A1 | 1/2003 |
|---|---|---|
| WO | 2004085378 A1 | 10/2004 |
| WO | 2010099501 A2 | 9/2010 |
| WO | WO 2012150328 A1 * | 11/2012 |

OTHER PUBLICATIONS

Herrmann, A.T., et al. "A Simple Method for Asymmetric Trifluoromethylation of N-Acyl Oxazolidinones via Ru-Catalyzed Radical Addition to Zirconium Enolates." J. Am. Chem. Soc. (2012), vol. 134, pp. 6976-6979.*

Hansen et al.; "Highly Efficient Asymmetric Synthesis of Sitagliptin"; Journal of the American Chemical Society; 2009; pp. 8798-8804.

Evans et al.; "A General Method for the Synthesis of Enantiomerically Pure β-Substituted, β-Amino Acids Through α-Substituted Succinic Acid Derivatives"; Journal of Organic Chemistry; 1999; pp. 6411-6417.

International Search Report for PCT/EP2012/058221; Dated Dec. 9, 2012.

* cited by examiner

*Primary Examiner* — Andrew D Kosar
*Assistant Examiner* — John S Kenyon
(74) *Attorney, Agent, or Firm* — Abelman, Frayne & Schwab

(57) ABSTRACT

A novel process is described for the synthesis of Sitagliptin, IUPAC name 7-[(3R)-3-amino-1-oxo-4-(2,4,5-trifluorophenyl)butyl]-5,6,7,8-tetrahydro-3-(trifluoromethyl)-1 2,4-triazolo[4,3-a]pyrazine, of formula (I).

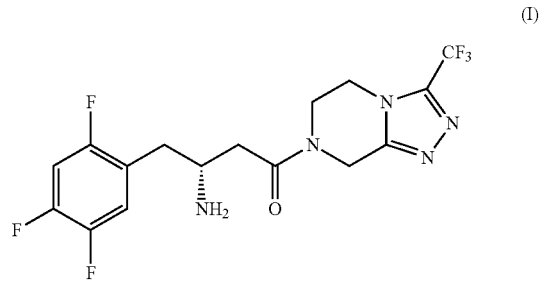

(I)

19 Claims, No Drawings

PROCESS FOR THE PRODUCTION OF SITAGLIPTIN

CROSS-REFERENCE TO RELATED APPLICATIONS

This application is a National Phase of PCT/EP2012/058221, filed 4 May, 2012 which claims the priority of Italian Application No. MI2011A000765, filed 5 May 2011, all of which are incorporated herein by reference.

FIELD OF THE INVENTION

The present invention relates to a process for the industrial production of Sitagliptin.

STATE OF THE ART

Sitagliptin, 7-[(3R)-3-amino-1-oxo-4-(2,4,5-trifluorophenyl)butyl]-5,6,7,8-tetrahydro-[3-(trifluoromethyl)-1,2,4-triazolo[4,3-a]pyrazine (I) according to IUPAC nomenclature, is characterised by the following structure:

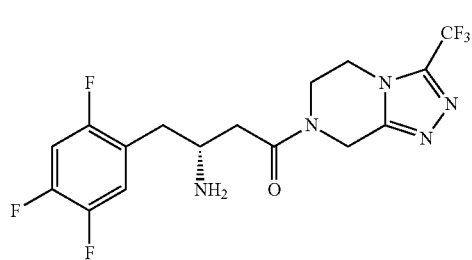

(I)

International patent application WO 03/004498 A1 and U.S. Pat. No. 6,699,871 B1, both assigned to Merck & Co., describe a class of β-amino tetrahydrotriazolo[4,3-a]pyrazines that are hypoglycemic agents and inhibitors of dipeptidyl peptidase IV. In these patents, molecules are generally claimed having the structure:

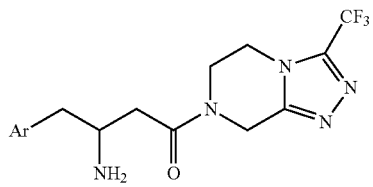

The compound 7-[(3R)-3-amino-1-oxo-4-(2,4,5-trifluorophenyl)butyl]-5,6,7,8-tetrahydro-[3-(trifluoromethyl)-1,2,4-triazolo[4,3-a]pyrazine (I) is specifically claimed in patent application WO 03/004498, in addition to a specific method for the production of Sitagliptin or a salt thereof, as shown in the scheme below:

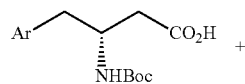

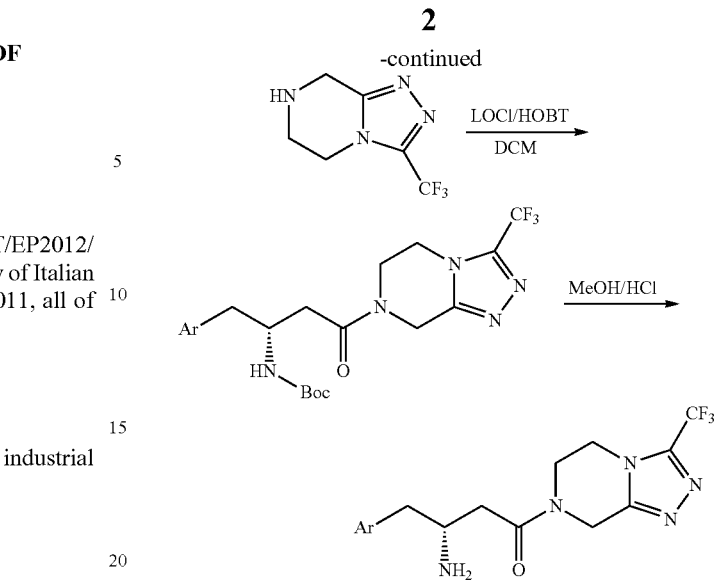

However, in said process, both the overall chemical yield and the percentage of product with the correct stereocentric configuration are particularly low. An improved synthetic method for the preparation of compound (I) is described in "Highly Efficient Asymmetric Synthesis of Sitagliptin", K. B. Hansen et al.: *Journal of the American Chemical Society* (2009), 131(25), 8798-8804 and in international patent application WO 2004/085378 A1. The key step in the process involves the stereoselective hydrogenation of a prochiral enamine in the presence of a complex formed between a transition metal and a chiral phosphine derived from ferrocene, according to the diagram:

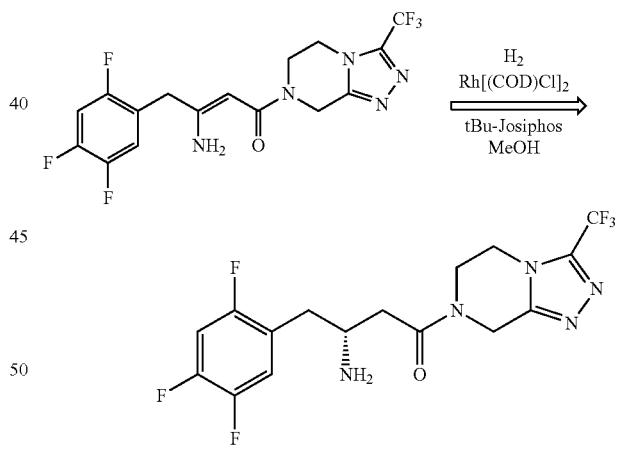

This process makes it possible to obtain the end product with good yield and a satisfactory enantiomeric excess, but requires the use of rhodium or iridium-based catalysts, which due to their extremely high cost, necessitate appropriate recovery methods that are not always simple.

A further synthetic improvement in the industrial preparation of Sitagliptin is described in international patent application WO 2010/099501 A2, which claims the use of a recombinant enzyme to perform direct transamination starting from the corresponding ketone. This synthetic method is probably the most advantageous one among those currently known. However, the biocatalytic technology used necessitates additional bacterial culture preparation and maintenance steps, or isolation of the enzyme of interest from the bacterial culture itself. These operations are normally problematic for a pharmaceutical active ingredient manufacturing industry.

A very effective process for obtaining derivatives of β-aminoacids is described in the article "A General Method for the Synthesis of Enantiomerically Pure β-Substituted, β-Amino Acids through α-Substituted Succinic Acid", D. A. Evans et al.: *Journal of Organic Chemistry* (1999), 64(17), 6411-6417. In this document, the key step in the process involves an alkylation of the enolate of a chiral acyloxazolidinone with an ester of a haloacetic acid, followed by a Curtius reaction.

SUMMARY OF THE INVENTION

The applicant has found a process for obtaining compound (I) characterised by highly crystalline products, and therefore easily isolable and purifiable with a degree of chemical and optical purity compatible with the standards imposed by the Pharmacopoeia, and with excellent overall reaction yields.

The process of the invention comprises the following steps:

a) alkylating an acyloxazolidinone of formula (II), containing an Evans' chiral auxiliary, with an alkylhaloacetate or a benzylhaloacetate of formula $XCH_2COOR^4$, obtaining an intermediate compound (III):

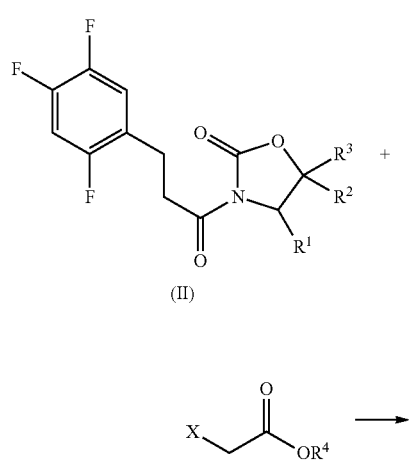

b) cleaving the Evans' chiral auxiliary from intermediate (III), obtaining the corresponding acid (IV):

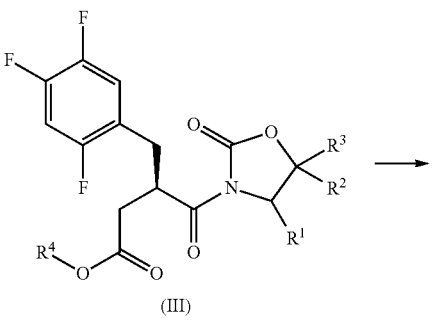

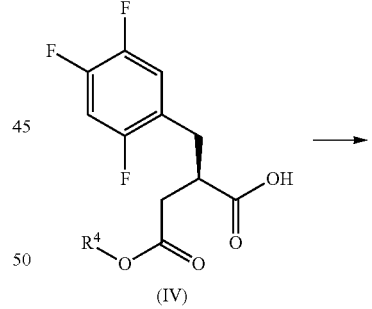

c) transforming acid (IV) into the isocyanate (V) which, treated with an alkyl or arylalkyl alcohol $R^5OH$, leads to the formation of the corresponding carbamate (VI):

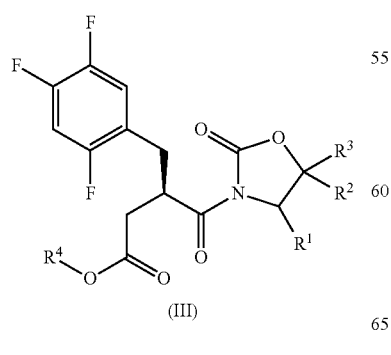

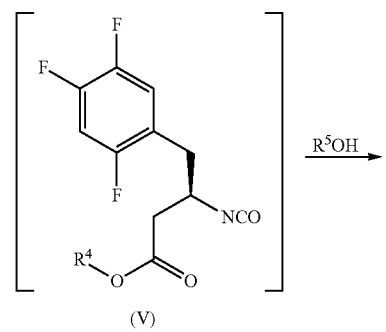

-continued

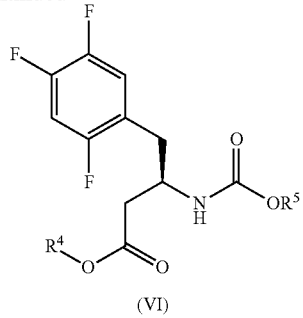

(VI)

d) selectively deprotecting the ester group of the carbamate (VI), obtaining the corresponding acid (VII):

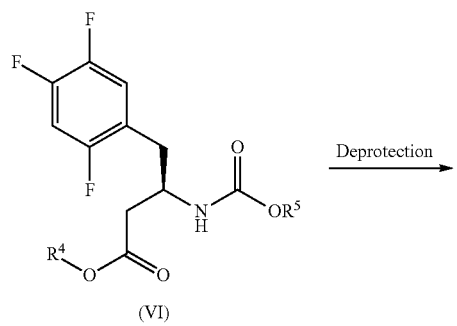

e) condensing the thus obtained acid (VII) with triazolopiperazine (VIII) to yield the carbamate (IX):

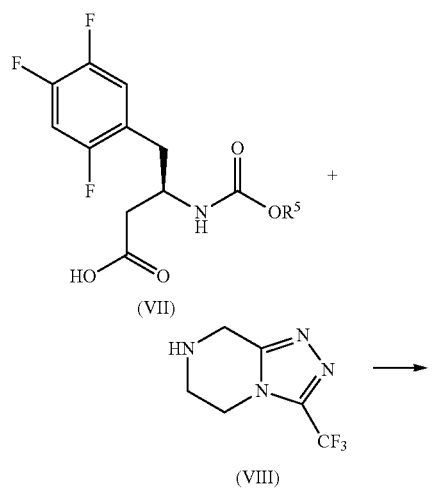

-continued

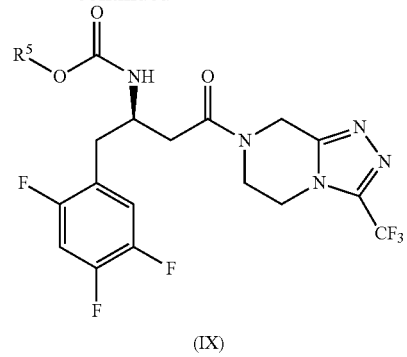

(IX)

f) transforming carbamate (IX) into Sitagliptin (I):

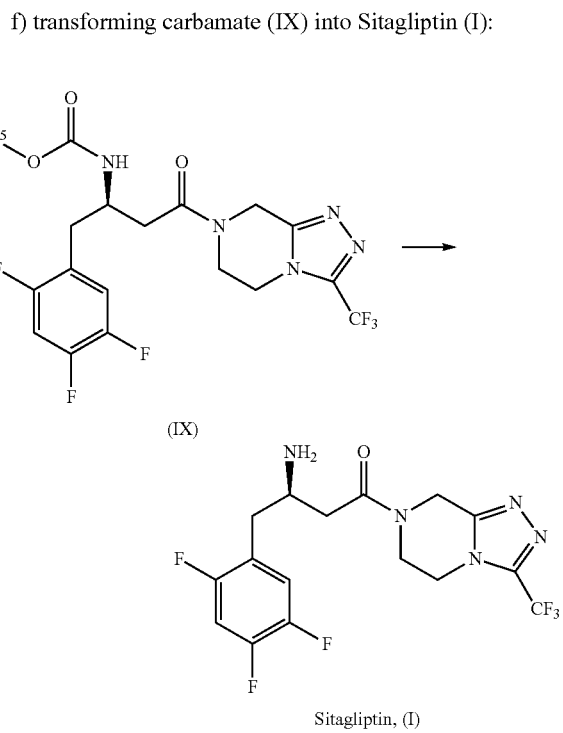

Further objects of the invention are the novel intermediates (II'), (III') and (IV'), compounds corresponding to the formulae (II), (III) and (IV) reported above, with substituents from $R^1$ to $R^4$ having particular meanings, as detailed below.

DETAILED DESCRIPTION OF THE INVENTION

The starting compound of the synthetic process of the present invention is the acyloxazolidinone of formula (II); this compound may be produced as a preliminary to the process of the invention, as described below.

Step a) of the process according to the invention consists in the alkylation of compound (II) with an alkylhaloacetate or benzylhaloacetate of formula X—CH$_2$—COOR$^4$, wherein X indicates a halogen (preferred compounds are tert-butyl bromoacetate and benzyl bromoacetate), in a quantity within the range of 1-1.5 equivalents with respect to the acyloxazolidinone and at a temperature varying between −78 and −30° C. (preferably between −45 and −35° C.).

The reactive form of the acyloxazolidinone is the enolate, which is prepared from compound (II) in a suitable solvent, preferably an ether, by treatment with a strong base, such as an amide of Na, Li or K; for example, it is possible to use lithium diisopropylamide (LDA), sodium hexamethyldisilazide (NaHMDS), potassium hexamethyldisilazide (KHMDS) or lithium hexamethyldisilazide (LiHMDS), in a quantity within the range of 1-1.5 equivalents (with respect to compound (II)). Preferably, the base used is LiHMDS in a quantity of 1.1 equivalents.

It is known that the Evans' auxiliary present in compound (II) is capable of highly efficiently directing the stereochemistry of the chiral centre formed in this reaction (high enantiomeric excess); the stereochemistry induced by the Evans' auxiliary depends on its original configuration (R or S), which may be determined once the substituents $R^1$, $R^2$ and $R^3$ are known. Independently of one another, these substituents may be hydrogen (with the condition that at most two of the substituents $R^1$, $R^2$ and $R^3$ are hydrogen simultaneously), a $C_1$-$C_6$ alkyl group (for example methyl, isopropyl or t-butyl), aromatic (e.g., phenyl) or alkylaromatic (e.g., benzyl) group; the preferred compound for the purposes of the invention is 4-(S)-benzyloxazolidin-2-one ($R^1$=benzyl, $R^2$, $R^3$=hydrogen).

This procedure makes it possible to obtain compound (III), a highly crystalline solid, characterised by a diastereomeric excess equal to at least 99% by HPLC; the diastereomeric excess may be improved to a value in excess of 99.5% by means of purification by crystallisation.

Subsequently, step b), the synthetic scheme envisages the cleavage of the Evans' chiral auxiliary of compound (III) to obtain the corresponding carboxylic acid (IV); this reaction occurs by treatment with an alkaline hydroxide such as, for example, those of sodium, lithium and potassium (preferably lithium hydroxide), in the presence of an appropriate quantity of hydrogen peroxide in water, or in a water-organic solvent mixture, followed by acidification of the resulting solution to a pH of less than 2, for example using sulfuric acid.

Organic solvents that may be used in admixture with water are the ethers (preferably THF and dioxane) or acetonitrile in a ratio varying from 1:1 to 1:10 with respect to the volume of water used, preferably three volumes. This reaction is carried out at a temperature varying between −15 and 15° C., preferably at 0° C. By operating in this manner it is possible to recover a large proportion of the chiral auxiliary by means of simple extraction on completion of the cleavage reaction.

Step c) of the process is the transformation of the carboxylic acid (IV) into one of the corresponding alkyl or arylalkyl (preferably benzyl) carbamates by means of one of the methods known in the art (for example the Curtius reaction).

This step involves an activation of the carboxylic acid (IV) by transformation into the corresponding acyl chloride or the corresponding mixed anhydride according to one of the methods known to the person skilled in the art, followed by a reaction with an azide of sodium or potassium in order to obtain the corresponding acylazide; the same transformation may be more advantageously obtained by direct reaction of the carboxylic acid (IV) with diphenylphosphoryl azide (DPPA) in the presence of an organic base such as a tertiary amine. On heating, the azide loses a molecule of nitrogen and rearranges into the isocyanate (V); if the reaction is conducted in the presence of an alcohol, $R^5OH$, the end result is the carbamate of formula (VI). Alcohols useful for the purpose of the present invention are 2,2,2-trichloroethanol, allyl alcohol, tert-butanol, methanol, ethanol, isopropanol and, preferably, benzyl alcohol.

The reaction may be carried out in an inert solvent such as THF, or preferably in toluene; in this case, the quantity of alcohol used may vary between 1 equivalent (with respect to the quantity of acid) and a quantity equal in volume to the quantity of solvent used for the reaction.

In the case of direct transformation of the carboxylic acid into azide, the molar quantity of DPPA, with respect to the acid, may vary between 1 and 2 equivalents (preferably 1.1 equivalents). The tertiary amine may be diisopropylamine, N-methylmorpholine, tributylamine, or preferably triethylamine.

The Curtius reaction is conducted at a temperature within the range from 50° C. to the boiling point of the solvent, and preferably between 70 and 110° C.

Step d) of the process is the cleavage of the ester group of the carbamate (VI), giving the corresponding acid (VII). This operation may be conducted according to one of the methods known in the field, such as those reported in Theodora W. Green, *Protective Groups in Organic Synthesis*, John Wiley & Sons (1999). In particular, deprotection of the acid group must be conducted under conditions orthogonal to those of the amine; selection of the particular reaction conditions depends on the nature of the two groups $R^4$ and $R^5$, and may be easily determined by one skilled in the art; purely by way of example, in the case that are $R^4$=t-butyl and $R^5$=benzyl, this step may be performed by treatment with a mixture of phosphoric acid (preferably 85%) and toluene in a w/w ratio equal to 1 with respect to the ester, or by treatment with a 1 to 1 mixture of trifluoroacetic acid (TFA) and methylene chloride, or else by treatment with formic acid at a temperature variable between 20 and 60° C., preferably 40° C.

Step e) of the process is the condensation of the acid (VII) with the triazolopiperazine (VIII), with formation of an amide bond, to obtain the carbamate (IX).

This reaction may be carried out according to various methods.

One first possibility is the activation of the carboxylic acid with carbonyldiimidazole, then adding the triazolopiperazine (VIII) to the reaction mixture. The reaction is carried out in an inert solvent such as, for example, acetonitrile, dimethylacetamide, or preferably THF. In the carboxylic acid activation phase, the temperature is maintained between 0 and 25° C., while in the reaction phase envisaging condensation with the triazolopiperazine (VIII), the temperature is maintained between 50° C. and the boiling point of the solvent. Alternatively, it is possible to use a salt of triazolopiperazine (VIII) (preferably the hydrochloride), adding however an appropriate base to the reaction mixture, for example a tertiary amine such as triethylamine. Finally, another possibility for achieving the condensation is to use one of the coupling agents known in the field, for example dicyclohexylcarbodiimide (DCC) or 1-ethyl-3-(3-dimethylaminopropyl) carbodiimmide (EDC), with the optional addition of further additives such as, for example, N-hydroxybenzotriazole (HOBT).

Finally, the last step in the process of the invention, f) provides for removal of the carbamate group present in compound (IX), to obtain the corresponding free amine and hence Sitagliptin (I). This step may be carried out according to one of the methods known in the field, such as those reported in Theodora W. Green, *Protective Groups in Organic Synthesis*, John Wiley & Sons (1999).

Compounds (II'), (III') and (IV'), produced as intermediates over the course of the synthetic process, are novel and constitute further objects of the invention.

As previously mentioned, the starting compound, the acyloxazolidinone of formula (II), may be produced as a preliminary to the process of the invention, according to various possible synthetic pathways.

One of these is represented in the following synthetic scheme:

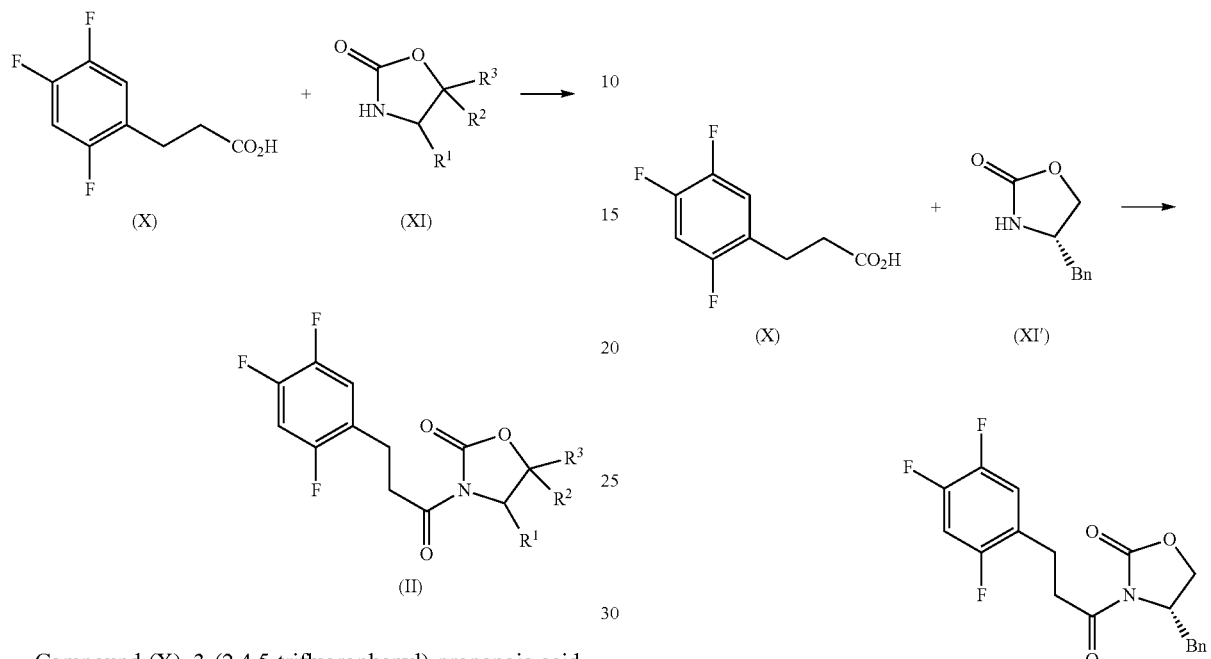

Compound (X), 3-(2,4,5-trifluorophenyl)-propanoic acid, is commercially available and sold for example by Acesys Pharmatech Co. Ltd., North Brunswick, N.J. (USA), or by JRD Fluorochemicals Ltd., Randalls Road, Leatherhead, Surrey, GB; alternatively, the acid (X) may be produced using methods that will be obvious to those skilled in the art.

The production of compound (II) entails the condensation of acid (X) with the Evans' chiral auxiliary (XI). The substituents $R^1$, $R^2$ and $R^3$ have the meanings given above. In the reaction, the Evans' auxiliary (XI) may be used as it is, or in the form of the Li, Na or K salt thereof, obtained therefrom by treatment with a strong base.

In the case, for example, of use of the Evans' auxiliary in the form of a lithium salt, the oxazolidinone (XI), solubilised in an appropriate solvent (preferably an ether), is treated with an organolithium compound and subsequently subjected to an acylation reaction by treatment with an acyl chloride, a mixed anhydride or a symmetrical anhydride, prepared in advance starting from the carboxylic acid (X) according to methods known in the field.

This step may alternatively and preferably be carried out by treating the acid (X), solubilised in an appropriate solvent (preferably an ether), with pivaloyl chloride (or a compound equivalent thereto for the preparation of mixed anhydrides), in the presence of a tertiary amine (preferably triethylamine) to form the corresponding mixed anhydride (optionally isolable) and treating the latter with the oxazolidinone and optionally a lithium salt (preferably LiCl).

These two different processes result in obtaining with excellent yields the product (II), a highly crystalline solid, and therefore easily purifiable.

The invention will be further illustrated by the following examples.

EXAMPLE 1

Synthesis of (S)-4-benzyl-3-(3-(2,4,5-trifluorophenyl)propanoyl)oxazolidin-2-one (II'), compound of formula (II) wherein $R^1$=benzyl (Bn) and $R^2$, $R^3$=hydrogen

EXAMPLE 1A

In a first reaction flask fitted with magnetic stirrer and thermometer, and under an inert atmosphere of $N_2$, thionyl chloride (0.9 mL, 12.96 mmol) is added to the acid (X) (2.00 g, 9.79 mmol) and magnetically stirred at 30° C. for 1 hour. The solvent is then evaporated under reduced pressure and the thionyl chloride and HCl residues are removed by co-evaporation with toluene.

In a second reaction flask fitted with magnetic stirrer and thermometer, and under an inert atmosphere of $N_2$, the 4-(S)-benzyloxazolidin-2-one of formula (XI'), compound of formula (XI) wherein $R^1$=benzyl and $R^2$, $R^3$=hydrogen (1.72 g, 9.70 mmol) is solubilised in THF (18 mL) at −5° C., then hexyllithium is added dropwise (2.3 M solution in hexane, 4.2 mL, 9.66 mmol). On completion of the addition, the content of the first reaction flask dissolved in 5 mL of THF is added at the same temperature and magnetically stirred, between −10° C. and 0° C., until the starting material has disappeared.

On completion of the reaction, 25 mL of water is added and the mixture is extracted with toluene (20 mL). The combined organic phases are dried and evaporated under reduced pressure. 3.20 g of a brown oil is obtained. The product is purified by crystallisation from MeOH (60% yield).

$^1$H NMR (300 MHz, $CDCl_3$) δ 7.35-7.26 (m, 3H), 7.21-7.07 (m, 3H), 6.89 (ddd, $J_1$=$J_2$=6.7, $J_3$=9.8 Hz, 1H), 4.70-4.61 (m, 1H), 4.22-4.14 (m, 2H), 3.30-3.18 (m, 3H), 2.98 (t, J=7.3 Hz, 2H), 2.76 (dd, $J_1$=9.5, $J_2$=13.2 Hz, 1H).

EXAMPLE 1B

In a reaction flask fitted with magnetic stirrer and thermometer, and under an inert atmosphere of $N_2$, the Evans' oxazolidinone (XI') (4.33 g, 24.5 mmol), the acid (X) (5.00 g, 24.5 mmol) and LiCl (2.07 g, 49.0 mmol) are solubilised in THF (75 mL) and the temperature of the mixture adjusted to −20° C., temperature at which pivaloyl chloride (4.5 mL, 36.8 mmol) and, dropwise, triethylamine (6.8 mL, 49.0 mmol), are added. The mixture is magnetically stirred, keeping the temperature below −20° C., until the starting material has disappeared.

On completion of the reaction, a saturated solution of NH$_4$Cl is added and the THF evaporated under reduced pressure, and the reaction mixture is extracted using toluene. The combined organic phases are dried and evaporated under reduced pressure.

The product is purified by crystallisation from isopropanol (6.41 g, 72% yield).

EXAMPLE 2

Synthesis of (R)-t-butyl-4-((S)-4-benzyl-2-oxo-oxazolidin-3-yl)-4-oxo-3-(2,4,5-trifluorobenzyl)butanoate (III'), compound of formula (III) wherein R$^1$=benzyl, R$^2$, R$^3$=hydrogen, R$^4$=t-butyl and X=Br

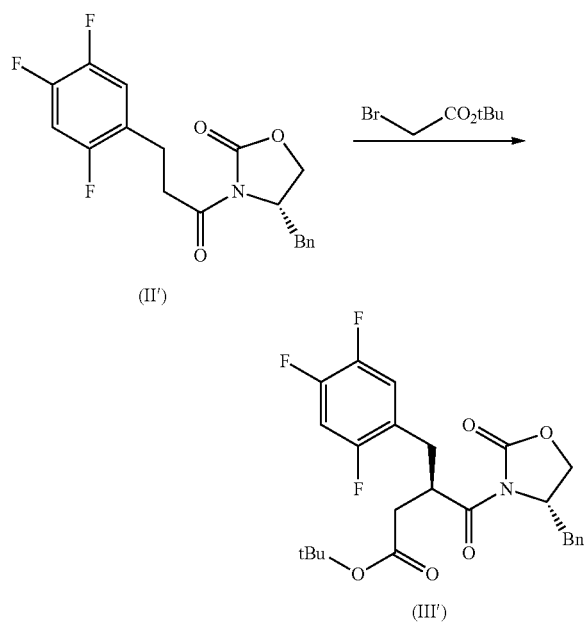

EXAMPLE 2A

In a reaction flask fitted with magnetic stirrer and thermometer, and under an inert atmosphere of N$_2$, diisopropylamine (0.4 mL, 3.38 mmol) is solubilised in THF (4 mL). The temperature of the solution thus obtained is adjusted to −30° C., at which temperature hexyllithium (2.3 M solution in hexane, 1.3 mL, 3.02 mmol) is added dropwise and magnetically stirred for 20 minutes at the same temperature. The reaction mixture is then cooled to −78° C., and a solution of oxazolidinone (II') (1.00 g, 2.75 mmol) in THF is added dropwise at the same temperature, followed after 10 minutes by dropwise addition of t-butyl bromoacetate (0.4 mL, 3.02 mmol).

The temperature is allowed to rise gradually to −15° C. and, on completion of the reaction, the reaction mixture is poured into a mixture of water and acetic acid (4:1) and extracted with toluene. The combined organic phases are dried and evaporated under reduced pressure (HPLC of the crude product shows a diastereomeric ratio of 99:1 RS/SS). The product is purified by flash chromatography (30% yield) showing a diastereomeric ratio in excess of 99.5%.

$^1$H NMR (300 MHz, CDCl$_3$) δ 7.38-7.23 (m, 5H), 7.22-7.13 (m, 1H), 6.89 (ddd, J$_1$=J$_2$=6.7, J$_3$=9.8 Hz, 1H), 4.69-4.58 (m, 1H), 4.42-4.32 (m, 1H), 4.18-4.12 (m, 2H), 3.32 (dd, J$_1$=3.1, J$_2$=13.0 Hz, 1H), 2.92-2.70 (m, 5H), 2.34 (dd, J$_1$=4.3, J$_2$=17.0 Hz, 1H), 1.41 (s, 9H).

EXAMPLE 2B

In a reaction flask fitted with magnetic stirrer and thermometer, and under an inert atmosphere of N$_2$, the oxazolidinone (II') (2.00 g, 5.50 mmol) is solubilised in THF (20 mL). The temperature is lowered to −78° C., and NaHMDS (1.0 M solution in THF, 6.0 mL, 6.00 mmol) and t-butyl bromoacetate (2.4 mL, 18.15 mmol) are added dropwise.

On completion of the reaction, water (5 mL) is added and the mixture extracted with toluene. The combined organic phases are dried and evaporated under reduced pressure (HPLC of the crude product shows a diastereomeric ratio of 98:2 RS/SS). The product, compound (III'), is purified by crystallisation from isopropanol (1.36 g, 52% yield) showing a diastereomeric ratio in excess of 99.5%.

EXAMPLE 2C

In a reaction flask fitted with magnetic stirrer and thermometer, and under an inert atmosphere of N$_2$, the oxazolidinone (II') (2.00 g, 5.50 mmol) is solubilised in THF (12 mL). The mixture is cooled to −40° C., and LiHMDS (1.0 M solution in THF, 6.0 mL, 6.00 mmol) is added dropwise, followed by slow addition of t-butyl bromoacetate (2.4 mL, 16.51 mmol).

On completion of the reaction, water (5 mL) is added and the mixture extracted with isopropyl acetate. The combined organic phases are dried and evaporated under reduced pressure (HPLC of the crude product shows a diastereomeric ratio of 99:1 RS/SS). The product, compound (III'), is purified by crystallisation from isopropanol (1.93 g, 72% yield) showing a diastereomeric ratio in excess of 99.5%.

EXAMPLE 3

Synthesis of (R)-4-(t-butoxy)-4-oxo-2-(2,4,5-trifluorobenzyl)butanoic acid (IV'), compound of formula (IV) wherein R$^4$=t-butyl

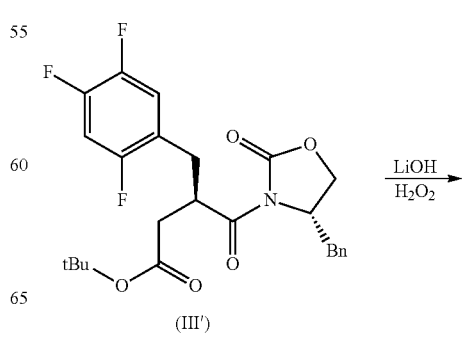

-continued

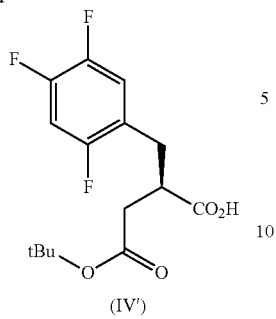

In a reaction flask fitted with magnetic stirrer and thermometer, and under an inert atmosphere of $N_2$, the oxazolidinone (III') (650 mg, 1.36 mmol) is solubilised in THF (10 mL) at 0° C., then 35% w/w hydrogen peroxide (0.4 mL, 5.43 mmol) and 4 mL of an aqueous solution of LiOH (65 mg, 2.71 mmol) are added. The reaction is monitored by TLC, eluting with AcOEt-Hexane 3:7 and developing with $KMnO_4$. On completion of the reaction, a saturated solution of sodium bisulphite is added and the mixture extracted using dichloromethane. The acid (IV') is obtained, which is first purified by extraction with aqueous sodium hydroxide and washing of the aqueous solution with dichloromethane in order to eliminate the Evans' chiral auxiliary (purifiable by crystallisation from heptane), then by acidification of the aqueous solution to pH=1 with sulfuric acid followed by extraction with dichloromethane.

The combined organic phases are dried and evaporated under reduced pressure. The product (389 mg, 90% yield), a crystalline white solid, shows an enantiomeric ratio by chiral HPLC in excess of 99.5%.

$^1$H NMR (300 MHz, $CDCl_3$) δ 10.7 (bs, 1H), 7.02 (ddd, $J_1$=7.0, $J_2$=8.6, $J_3$=10.4 Hz, 1H), 6.89 (ddd, $J_1$=$J_2$=6.7, $J_3$=9.8 Hz, 1H), 3.12-2.95 (m, 2H), 2.82 (dd, $J_1$=6.7, $J_2$=13.0 Hz, 1H), 2.56 (dd, $J_1$=8.0, $J_2$=16.0 Hz, 1H), 2.38 (dd, $J_1$=5.2, $J_2$=16.5 Hz, 1H), 1.41 (s, 9H).

EXAMPLE 4

Synthesis of (R)-tert-butyl 3-(((benzyloxy)carbonyl) amino)-4-(2,4,5-trifluorophenyl) butanoate (VI'), compound of formula (VI) wherein $R^4$=t-butyl and $R^5$=benzyl -continued

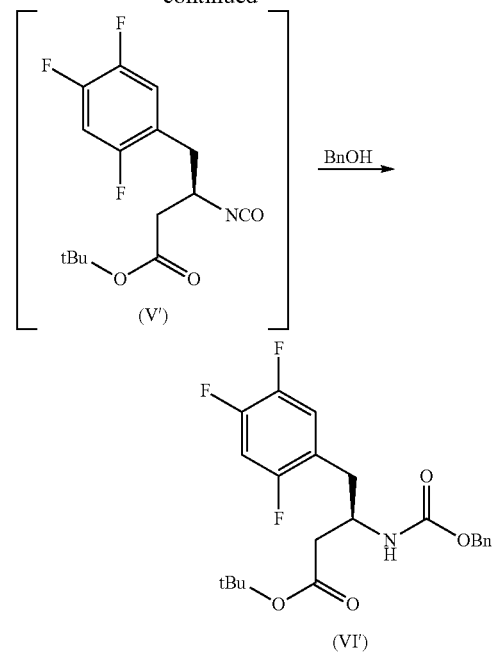

To the acid (IV') (820 mg, 2.58 mmol) solubilised in toluene (8 mL) is added triethylamine (0.4 mL, 2.70 mmol), and then the mixture is heated to 80° C. Diphenylphosphoryl azide (0.56 mL, 2.58 mmol) is then added dropwise, followed 30 minutes later by benzyl alcohol (0.3 mL, 2.58 mmol).

The reaction mixture is refluxed for 3 hours, then water (16 mL) is added and the mixture extracted with toluene.

The combined organic phases are dried and evaporated under reduced pressure. The product, compound (VI'), is purified by crystallisation from a $MeOH/H_2O$ mixture (80% yield).

$^1$H NMR (300 MHz, $CDCl_3$) δ 7.38-7.24 (m, 5H), 7.08-6.96 (m, 1H), 6.92-6.80 (m, 1H), 5.45 (d, J=8.8 Hz, 1H), 5.04 (d, J=2.0 Hz, 2H), 4.23-4.09 (m, 1H), 2.86 (d, J=6.7 Hz, 2H), 2.44 (dq, $J_1$=5.2, $J_2$=16.2 Hz, 2H), 1.45 (s, 9H).

EXAMPLE 5

Synthesis of (R)-3-(((benzyloxy)carbonyl)amino)-4-(2,4,5-trifluorophenyl)butanoic acid (VII'), compound of formula (VII) wherein $R^5$=benzyl

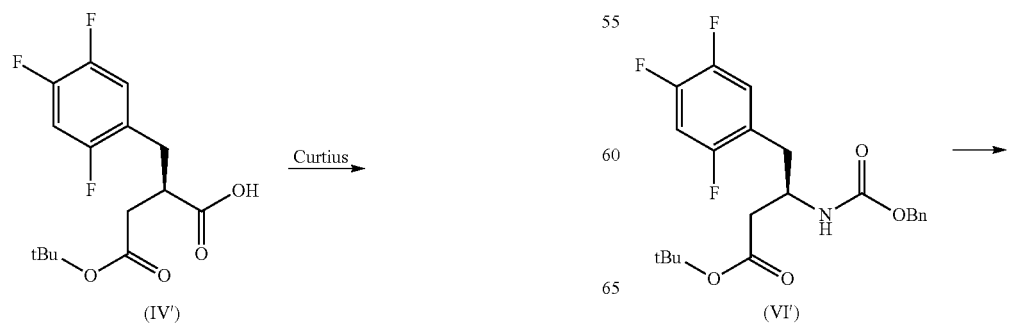

EXAMPLE 5A

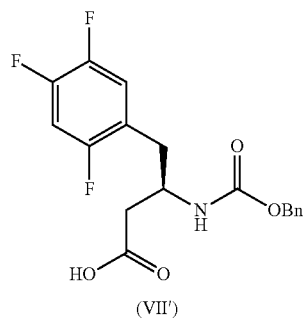

(VII')

In a reaction flask fitted with magnetic stirrer and thermometer, and under an inert atmosphere of $N_2$, the t-butyl ester (VI') (2.00 g, 4.72 mmol) is solubilised in trifluoroacetic acid (3 mL) at 0° C. The mixture is magnetically stirred at 0° C. for 5 hours until the starting material has disappeared, then $H_2O$ is added and the mixture is extracted with isopropyl acetate. The combined organic phases are washed with water, dried, and evaporated under reduced pressure.

1.38 g of a crystalline white solid is obtained, compound (VII') (80% yield).

$^1$H NMR (300 MHz, $d_6$-dmso) δ 7.38-7.24 (m, 5H), 7.07-6.97 (m, 1H), 6.91-6.82 (m, 1H), 6.0 & 5.34 (2×bs, 1H overall, 2 NH rotamers), 5.06 & 5.01 (AB system, J=11.6 Hz, 2×1H), 4.3-4.1 (m, 1H), 2.92-2.80 (m, 2H), 2.70-2.50 (m, 2H).

EXAMPLE 5B

In a reaction flask fitted with magnetic stirrer, thermometer and condenser, and under an inert atmosphere of $N_2$, the t-butyl ester (VI') (2.00 g, 4.72 mmol) is suspended in formic acid (2 mL). The mixture is warmed to 50° C. and magnetically stirred at the same temperature for 3 hours until the starting material has disappeared.

On completion of the reaction, the mixture is taken to room temperature, then $H_2O$ is added and the mixture extracted with isopropyl acetate. The combined organic phases are washed with water, dried and evaporated under reduced pressure. 1.38 g of a crystalline white solid is obtained, compound (VII') (80% yield).

$^1$H NMR (300 MHz, $d_6$-dmso) δ 7.38-7.24 (m, 5H), 7.07-6.97 (m, 1H), 6.91-6.82 (m, 1H), 6.0 & 5.34 (2×bs, 1H overall, 2 NH rotamers), 5.06 & 5.01 (AB system, J=11.6 Hz, 2×1H), 4.3-4.1 (m, 1H), 2.92-2.80 (m, 2H), 2.70-2.50 (m, 2H).

EXAMPLE 6

Synthesis of (R)-benzyl (4-oxo-4-(3-(trifluoromethyl)-5,6-dihydro-[1,2,4]triazolo[4,3-a]pyrazin-7(8H)-yl)-1-(2,4,5-trifluorophenyl)butan-2-yl)carbamate (IX'), compound of formula (IX) wherein $R^5$=benzyl

EXAMPLE 6A

To a solution of the acid (VII') (300 mg, 0.90 mmol) and triazolopiperazine (VIII) (170 mg, 0.90 mmol) in $CH_2Cl_2$ (10 mL) is added N-hydroxybenzotriazole (150 mg, 1.08 mmol), and 10 minutes later, EDC (260 mg, 1.35 mmol).

The mixture, under an inert atmosphere of $N_2$, is magnetically stirred for 4 hours until completion, then a saturated solution of sodium bicarbonate (5 mL) is added and the mixture is extracted with dichloromethane.

The combined organic phases are dried and evaporated under reduced pressure. The product is purified by flash chromatography, obtaining 406 mg (86% yield) of a crystalline white solid, compound (IX').

$^1$H NMR (300 MHz, $d_6$-dmso, 100° C.) δ 7.4-7.2 (m, 7H), 6.90 (bs, 1H) 4.97 & 4.90 (AB system, J=12.9 Hz, 2×1H), 4.92 (s, 2H), 4.26-4.14 (m, 3H), 3.97 (t, J=5.5 Hz, 2H), 2.92 & 2.67 (2×dd, J=14.1, 4.9 Hz, 2×1H), 2.83-2.72 (m, 2H).

EXAMPLE 6B

To a solution of the acid (VII') (1.00 g, 2.62 mmol) in THF (5 mL) at 0° C. is added carbonyldiimidazole (510 mg, 3.15 mmol) and 10 minutes later triethylamine (0.4 mL, 2.62 mmol), previously solubilised in THF (5 mL), and triazolopiperazine hydrochloride (VIII) (599 mg, 2.62 mmol).

The mixture, under an inert atmosphere of $N_2$, is magnetically stirred under reflux for 16 hours until completion, then the mixture is cooled to room temperature, water added and the mixture extracted with toluene.

The combined organic phases are dried and evaporated under reduced pressure.

$^1$H NMR (300 MHz, $d_6$-dmso, 100° C.) δ 7.4-7.2 (m, 7H), 6.90 (bs, 1H) 4.97 & 4.90 (AB system, J=12.9 Hz, 2×1H), 4.92 (s, 2H), 4.26-4.14 (m, 3H), 3.97 (t, J=5.5 Hz, 2H), 2.92 & 2.67 (2×dd, J=14.1, 4.9 Hz, 2×1H), 2.83-2.72 (m, 2H).

EXAMPLE 7

Synthesis of Sitagliptin

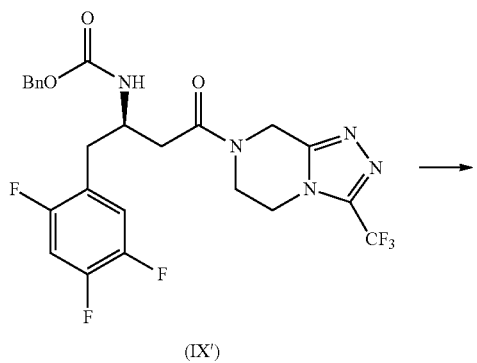

(IX')

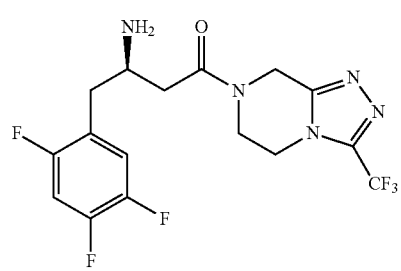

Sitagliptin, (I)

Pd/C (10% w/w, 50% water, 256 mg, 0.12 mmol) is added to a solution of the carbamate (IX') (1.30 g, 2.40 mmol) in THF (5 mL), then the mixture is hydrogenated under atmospheric pressure overnight at ambient temperature.

On completion of the reaction, the catalyst is filtered and the solution is concentrated under reduced pressure, forming Sitagliptin free base (white foam) in quantitative yield and showing an enantiomeric ratio by chiral HPLC in excess of 99.5%.

The invention claimed is:

1. A process for producing 7-[(3R)-3-amino-1-oxo-4-(2,4,5-trifluorophenyl)butyl]-5,6,7,8-tetrahydro-[3-(trifluoromethyl)-1,2,4-triazolo[4,3-a]pyrazine, Sitagliptin, of formula (I)

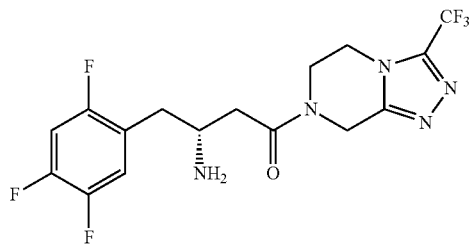

comprising the following steps:

a) alkylating an acyloxazolidinone of formula (II)

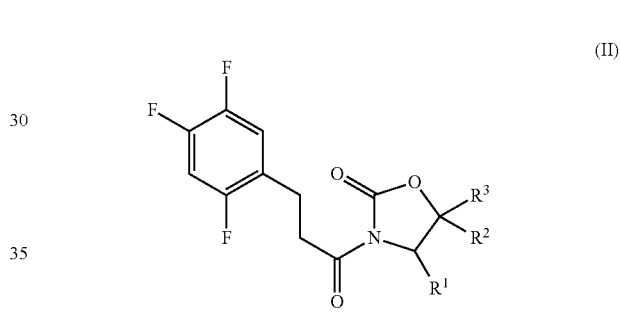

containing an Evans' chiral auxiliary, with an alkylhaloacetate or a benzylhaloacetate of formula XCH2COOR$^4$

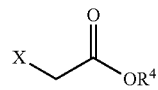

obtaining an intermediate compound (III):

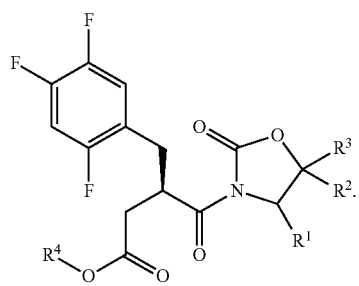

b) cleaving the Evans' chiral auxiliary from intermediate (III)

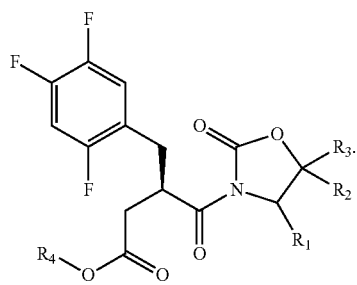

(III)

obtaining the corresponding acid (IV):

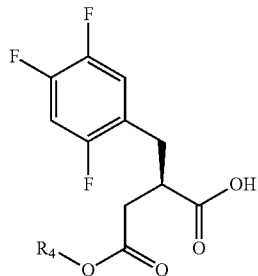

(IV)

c) transforming acid (IV)

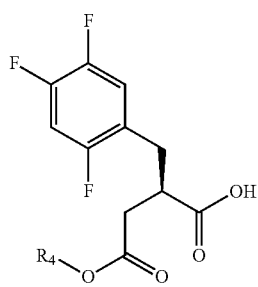

(IV)

into isocyanate (V),

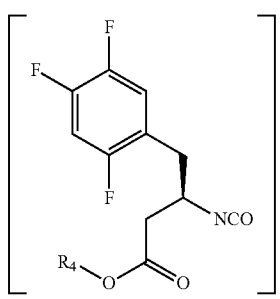

(V)

which treated with an alkylic or arylalkylic alcohol $R^5$—OH leads to the formation of the corresponding carbamate (VI):

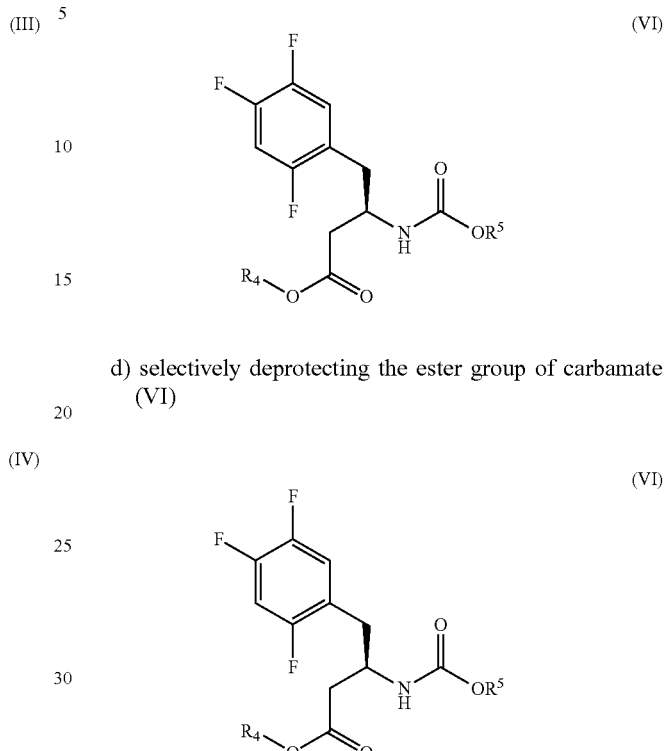

(VI)

d) selectively deprotecting the ester group of carbamate (VI)

(VI)

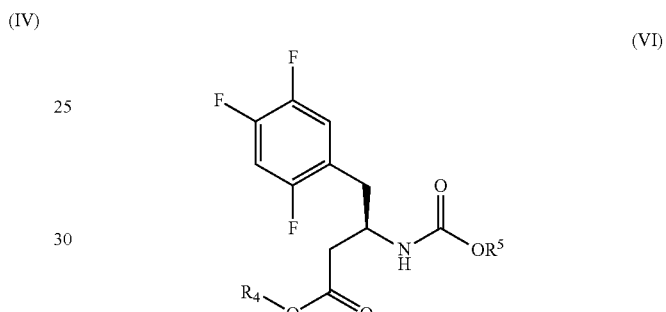

obtaining the corresponding acid (VII):

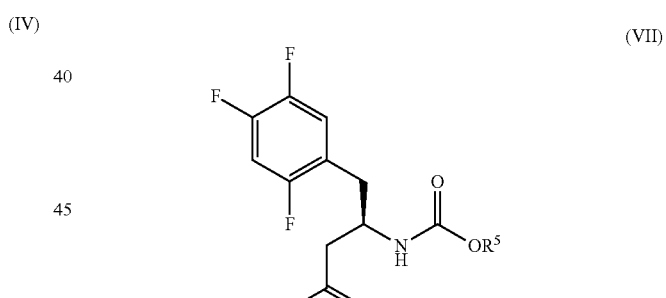

(VII)

e) condensing the thus obtained acid (VII)

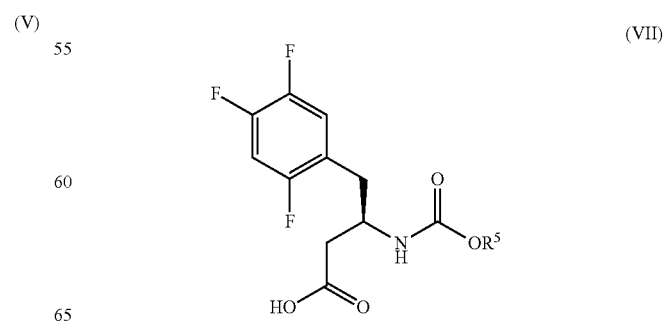

(VII)

with the triazolpiperazine (VIII)

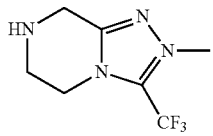
(VIII)

to yield carbamate (IX):

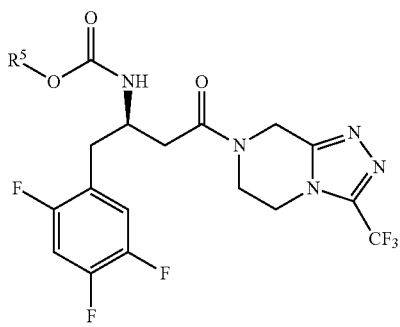
(IX)

f) transforming carbamate (IX)

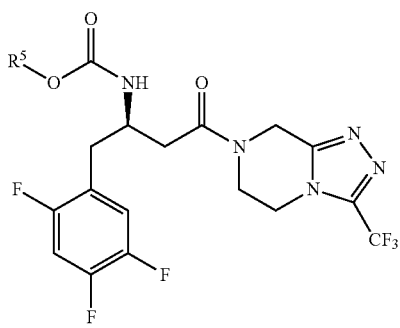
(IX)

into Sitagliptin (I):

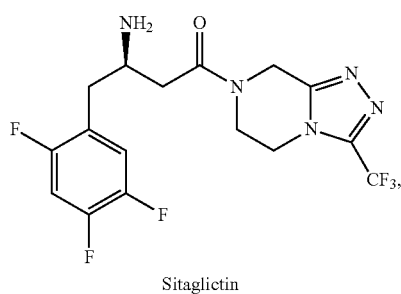
(I)

Sitaglictin in which $R^1$, $R^2$ and $R^3$ are, independently from each other, hydrogen, C1-C6 alkyl, or an aromatic or alkylaromatic group;

$R^4$ and $R^5$ are alkyl or benzyl; and

X is a halogen, with the provisos that:

at most two of the substituents $R^1$, $R^2$ and $R^3$ are simultaneously hydrogen; and when $R^4$ is alkyl, then $R^5$ is benzyl, and vice versa.

2. The process according to claim 1 wherein, in step a), acyloxazolidinone (II) is transformed into its enolate by treatment with a strong base, and alkylation occurs by reaction of said enolate with an alkylhaloacetate or a benzylhaloacetate, employed in an amount comprised between 1 and 1.5 equivalents with respect to the oxazolidinone, at a temperature comprised between −78 and −30° C.

3. The process according to claim 1, wherein step b) is carried out by treating compound (III) with an alkaline hydroxide in the presence of hydrogen peroxide in water or in a water-organic solvent mixture.

4. The process according to claim 1 wherein step c) is carried out at a temperature comprised between 50° C. and the boiling temperature of the solvent, and involves the phases of activating carboxylic acid (IV) by transformation into the corresponding acyl chloride or the corresponding mixed anhydride; reacting said chloride or anhydride with an azide, forming an acyl azide which rearranges into isocyanate (V); and reacting the isocyanate with an alcohol.

5. The process according to claim 1, wherein step c) is carried out by direct reaction of carboxylic acid (IV) with diphenylphosphoryl azide (DPPA) in the presence of an organic base.

6. The process according to claim 1, wherein the reaction of step e) is carried out in an inert solvent, activating carboxylic acid (VII) with carbonyldiimidazole at a temperature comprised between 0 and 25° C., and adding triazolpiperazine (VIII) and reacting at a temperature comprised between 50° C. and the boiling temperature of the solvent.

7. The process according to claim 1, wherein the reaction of step e) is carried out using a salt of triazolpiperazine (VIII) and adding a base to the reaction mixture.

8. The process according to claim 7, wherein said base is a tertiary amine.

9. The process according to claim 1, wherein the reaction of step e) is carried out using a condensing agent selected between dicyclohexylcarbodiimide and 1-ethyl-3-(3-dimethylaminopropyl) carbodiimide.

10. The process according to claim 9, wherein N-hydroxybenzotriazole is further employed as additive.

11. The process according to claim 1, further comprising condensing the Evans' chiral auxiliary (XI)

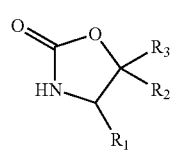
(XI)

with 3-(2,4,5-trifluorophenyl)-propanoic acid (X)

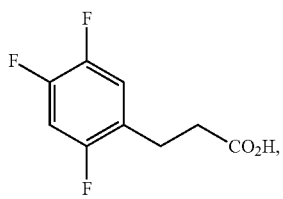
(X)

to produce the compound (II)

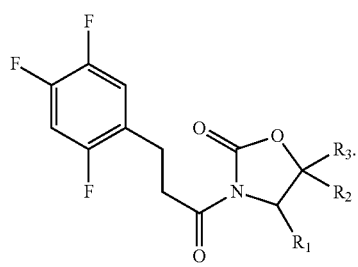
(II)

12. The process according to claim 11, wherein oxazolidinone (XI) is solubilized in a solvent, treated with a lithium-, sodium- or potassium-containing strong base and transformed into a salt of said metal, which is then reacted with a derivative of acid (X) selected among the acyl chloride, a mixed anhydride and a symmetrical anhydride.

13. The process according to claim 11, wherein acid (X) is solubilized in a solvent, treated with pivaloyl chloride in the presence of a tertiary amine obtaining the corresponding mixed anhydride, and the latter is treated with oxazolidinone (XI).

14. The process according to claim 13 wherein said mixed anhydride is treated with oxazolidinone (XI) and a lithium salt.

15. (R)-4-(tert-butoxy)-4-oxo-2-(2,4,5-trifluorobenzyl) butanoic acid, (IV).

16. Compound of general formula (II):
wherein $R^1$, $R^2$ and $R^3$ are, independently from each other, hydrogen, C1-C6 alkyl, or an aromatic or alkylaromatic group, with the proviso that at most two of the substituents $R^1$, $R^2$ and $R^3$ are simultaneously hydrogen.

17. Compound of general formula (III):
wherein $R^1$, $R^2$ and $R^3$ are, independently from each other, hydrogen, C1-C6 alkyl, or an aromatic or alkylaromatic group, with the proviso that at most two of the substituents $R^1$, $R^2$ and $R^3$ are simultaneously hydrogen; and $R^4$ is alkyl or benzyl.

18. Compound of general formula (V):

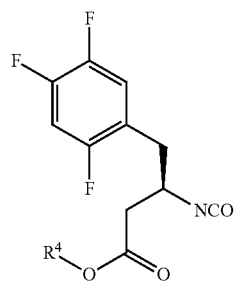
(V)

wherein $R^4$ is alkyl or benzyl.

19. (R)-tert-butyl-3-(((benzyloxy)carbonyl)amino)-4-(2,4,5-trifluorophenyl) butanoate, compound of formula (VI'):

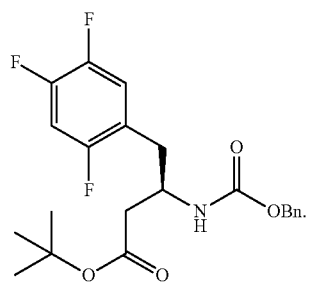
(VI')

* * * * *